United States Patent
Wu (10) Patent No.: US 11,033,650 B2
(45) Date of Patent: Jun. 15, 2021

(54) DECORATIVE COMBUSTION DEVICE CAPABLE OF EMITTING FRAGRANCE

(71) Applicant: Pro-Iroda Industries, Inc., Taichung (TW)

(72) Inventor: Wei Cheng Wu, Taichung (TW)

(73) Assignee: Pro-Iroda Industries, Inc., Taichung (TW)

( * ) Notice: Subject to any disclaimer, the term of this patent is extended or adjusted under 35 U.S.C. 154(b) by 103 days.

(21) Appl. No.: 16/505,809

(22) Filed: Jul. 9, 2019

(65) Prior Publication Data
US 2020/0338224 A1    Oct. 29, 2020

(30) Foreign Application Priority Data

Apr. 24, 2019 (TW) ................................. 108114262
Jun. 19, 2019 (TW) ................................. 108121255

(51) Int. Cl.
*A61L 9/03* (2006.01)
(52) U.S. Cl.
CPC .................................... *A61L 9/037* (2013.01)
(58) Field of Classification Search
None
See application file for complete search history.

(56) References Cited

U.S. PATENT DOCUMENTS

| | | | |
|---|---|---|---|
| 2,775,006 A * | 12/1956 | Kranc | A01M 1/2088 422/125 |
| 5,840,246 A | 11/1998 | Hammons et al. | |
| 5,840,257 A | 11/1998 | Bureau et al. | |
| 6,290,914 B1 | 9/2001 | LeJeune et al. | |
| 6,503,459 B1 | 1/2003 | Leonard et al. | |
| 6,663,838 B1 | 12/2003 | Soller et al. | |
| 6,857,869 B1 | 2/2005 | Sun | |
| 7,232,550 B1 | 6/2007 | Rodgers et al. | |
| 7,637,737 B2 | 12/2009 | Furner et al. | |
| 8,047,837 B2 * | 11/2011 | Furner | A01M 1/2088 431/291 |
| 10,238,097 B2 | 3/2019 | Sharma et al. | |
| 2006/0198768 A1 | 9/2006 | Gupte et al. | |
| 2009/0291400 A1 * | 11/2009 | Levy | F21S 13/12 431/120 |

(Continued)

FOREIGN PATENT DOCUMENTS

| | | |
|---|---|---|
| CA | 2181838 A1 | 1/1998 |
| CN | 2510064 Y | 9/2002 |

(Continued)

*Primary Examiner* — Jelitza M Perez
(74) *Attorney, Agent, or Firm* — Alan D. Kamrath; Karin L. Williams; Mayer & Williams PC (57) ABSTRACT

A combustion device comprises a burner and a fragrance diffuser. The burner is provided with a top end having a combustion portion. The fragrance diffuser includes a support and a holder adapted to hold a fragrance substance. The support is disposed on the top end and has an inner wall and an outer wall. The inner wall is arranged around the combustion portion, and the outer wall is arranged around the inner wall. A holding space is formed between the inner wall and the outer wall. The holder is disposed in the holding space. Thus, the combustion device is not only for decorative purpose, but also able to emit fragrance. Further, the fragrance diffuser can function as a windshield of the burner.

16 Claims, 10 Drawing Sheets

(56) References Cited

U.S. PATENT DOCUMENTS

| | | |
|---|---|---|
| 2010/0270391 A1 | 10/2010 | Allison et al. |
| 2013/0129571 A1 | 5/2013 | Chiu |
| 2014/0227141 A1* | 8/2014 | Chen ................ A61L 9/127 422/125 |
| 2015/0147707 A1 | 5/2015 | Hatfield |
| 2019/0082673 A1 | 3/2019 | Sharma et al. |

FOREIGN PATENT DOCUMENTS

| | | | |
|---|---|---|---|
| EP | 1216063 B1 | 5/2003 | |
| EP | 1310264 A1 * | 5/2003 | ............ A61L 9/037 |
| TW | 162832 | 7/1991 | |
| TW | M451141 U | 4/2013 | |
| WO | WO2017107229 A1 | 6/2017 | |

\* cited by examiner

DECORATIVE COMBUSTION DEVICE CAPABLE OF EMITTING FRAGRANCE

BACKGROUND

The present invention relates to a combustion device and, more particular, to a decorative combustion device capable of emitting fragrance.

Taiwan Utility Model Publication No. M451141 issued on Apr. 21, 2013 discloses a burner including a heating base having an accommodation space, a fragrance capsule placed in the accommodation space, and a covering member covering the fragrance capsule. The fragrance capsule includes a heat resistant container in contact with the heating base and having an opening, a fragrance block disposed in the heat resistant container, and a sealing cover sealing the opening to seal the fragrance block in the heat resistant container. In use, the sealing cover can be first torn, and then the heat resistant container with the fragrance block is placed in the accommodating space.

However, the foregoing burner used electric to heat the fragrance capsule to emit fragrance. It takes a very long time for the entire indoor space to be full of fragrance.

Thus, a need exists for a novel combustion device to mitigate and/or obviate the above disadvantages.

SUMMARY

In a first aspect, a combustion device according to the present invention comprises a burner and a fragrance diffuser. The burner is provided with a top end having a combustion portion. The fragrance diffuser includes a support and a holder adapted to hold a fragrance substance. The support is disposed on the top end and is provided with an inner wall and an outer wall. The inner wall extends in a vertical direction and is arranged around the combustion portion. The outer wall extends in the vertical direction and is arranged around the inner wall. A holding space is formed between the inner wall and the outer wall, and the holder is disposed in the holding space.

In an example, the burner is provided with a bottom end opposite to the top end. The burner includes a fuel container and a wick. The fuel container includes a wide portion adjacent to the bottom end, and a narrow portion adjacent to the top end. A width of the narrow portion is less than a width of the wide portion in a horizontal direction. An end of the narrow portion opposite to the wide portion is provided with an opening. A first end of the wick is inserted into the fuel container via the opening, and a second end of the wick is disposed in the combustion portion. The inner wall is arranged around the narrow portion, and an end of the inner wall adjacent to the burner is abutted against an outer end face located at a side of the wide portion adjacent to the narrow portion.

In an example, the support is provided with at least one connection rib extending in the vertical direction and disposed in the holding space. A first end of the at least one connection rib is connected to the inner wall, and a second end of the at least one connection rib is connected to the outer wall in the horizontal direction. The holder includes two recesses, and a hanging portion arranged between the two recesses. Two ends of the hanging portion are connected to the two recesses. The hanging portion hangs on a top edge of the at least one connection rib in the vertical direction. The two recesses are located at two opposite sides of the at least one connection rib.

In an example, the support includes four connection ribs respectively extending in the vertical direction and arrayed in the holding space in a circumferential direction at angles of equal intervals. A first end of each connection rib is connected to the inner wall, and a second end of each connection rib is connected to the outer wall in the horizontal direction. The hanging portion hangs on a top edge of one of the four connection ribs in the vertical direction. The two recesses are located at two opposite sides of one of the four connection ribs.

In an example, ends of the four connection ribs adjacent to the burner abut against the outer end face located at a side of the wide portion adjacent to the narrow portion. The outer wall is not in contact with the fuel container. The holding space is communicated with the outside via a gap formed between a bottom edge of the outer wall and the fuel container in the vertical direction.

In an example, the fragrance diffuser is provided with a lid abutting an end of the inner wall opposite to the burner in the vertical direction. The lid is provided with a through hole and a plurality of penetrating holes, and the through hole corresponds to the combustion portion. An end of the holding space is communicated with the outside via the plurality of penetrating holes.

In an example, an outer periphery of the lid corresponds to an inner periphery of the outer wall in the horizontal direction.

In an example, the support is formed as a single piece. The inner wall and the outer wall are round tubular and both extend along a central axis. The four connection ribs are sheet shapes.

In a second aspect, a combustion device according to the present invention comprises a burner and a fragrance diffuser. The burner is provided with a fuel container and an opening communicated with the fuel container. The burner includes a wick and a collar assembly. The wick is inserted into the fuel container via the opening. A ring body of the collar assembly includes a lower tube portion, an upper tube portion, and a flange. The lower tube portion and the upper tube portion are mounted around the wick. The lower tube portion is inserted into the opening. The upper tube portion extends out of the opening and is connected with the lower tube portion. The flange is radially connected outer peripheries of the lower tube portion and the upper tube portion and is disposed between the lower tube portion and the upper tube portion. The fragrance diffuser is mounted on a side of the flange opposite to the lower tube portion and is disposed adjacent to an outer periphery of the upper tube portion.

In an example, the fragrance diffuser includes a holder, a fragrance substance, and a lid. The holder is mounted on the side of the flange opposite to the lower tube portion and is disposed adjacent to the upper tube portion. A side of the holder opposite to the flange is provided with a recess. The fragrance substance is disposed in the recess. The lid is disposed on the side of the holder opposite to the flange and is provided with a through hole and a plurality of penetrating holes. The through hole is mounted around the upper tube portion. The plurality of penetrating holes correspond to the recess.

In an example, an end of the upper tube portion opposite to the lower tube portion is provided with a neck. A width of the neck is less than a maximum width of the upper tube portion in a radial direction. The lid is mounted around the neck and abuts against a stepped end face of the neck adjacent to the upper tube portion.

In an example, the ring body is formed as a single piece. The lower tube portion and the upper tube portion are round tubular and both extend along a central axis. The flange is an annular sheet.

In an example, the burner includes an inner wall and an outer wall. The fuel container and the opening are disposed at the inner wall. The outer wall is arranged around the inner wall. A hollow space is formed between the inner wall and the outer wall. A bottom edge of the outer wall is provided with an aperture communicated with the hollow space in a vertical direction. The burner is connected to a base mounted with the aperture. The base is provided with an open hole communicated with the hollow space. A first side of the base is provided with a slot disposed around the open hole, and the bottom edge is inserted into the slot.

In an example, a second side of the base is provided with a bottom portion. A first side of the slot opposite to the open hole is provided with an outer edge, and first height is formed between the outer edge and the bottom portion in the vertical direction. A second side of the slot adjacent to the open hole is provided with an inner edge and a second height is formed between the inner edge and the bottom portion in the vertical direction. The second height is less than the first height.

In an example, the inner wall and the outer wall are formed as a single piece.

In an example, an inner periphery of the outer wall is not in contact with an outer periphery of the inner wall. The inner wall includes a tubular containing portion and a connection tube portion. The fuel container is disposed in the containing portion. The connection tube portion is connected to the containing portion. The opening is disposed in the connection tube portion. The outer wall includes an outer tubular portion and a connection portion. The containing portion and the outer tubular portion both extend along a central axis. A first side of the connection portion is connected to an end of the connection tube portion opposite to the containing portion, and a second side of the connection portion is connected to a top end of the outer tubular portion in the vertical direction.

In an example, the collar assembly includes a plurality of O-rings. An outer periphery of the lower tube portion opposite to the wick is provided with a plurality of grooves. The plurality of the O-rings are respectively arranged in the plurality of grooves, and sides of the plurality of the O-rings opposite to the ring body abut against an inner periphery of the connection tube portion.

In an example, the inner wall and the outer wall are made of glass and are transparent. The wick is made of metal. The ring body is made of metal or plastic.

The present invention will become clearer in light of the following detailed description of illustrative embodiments of this invention described in connection with the drawings.

BRIEF DESCRIPTION OF THE DRAWINGS

The aforementioned and other aspects of the invention may best be understood by reference to the following description taken in conjunction with the accompanying drawings in which.

DETAILED DESCRIPTION

Figure 1:
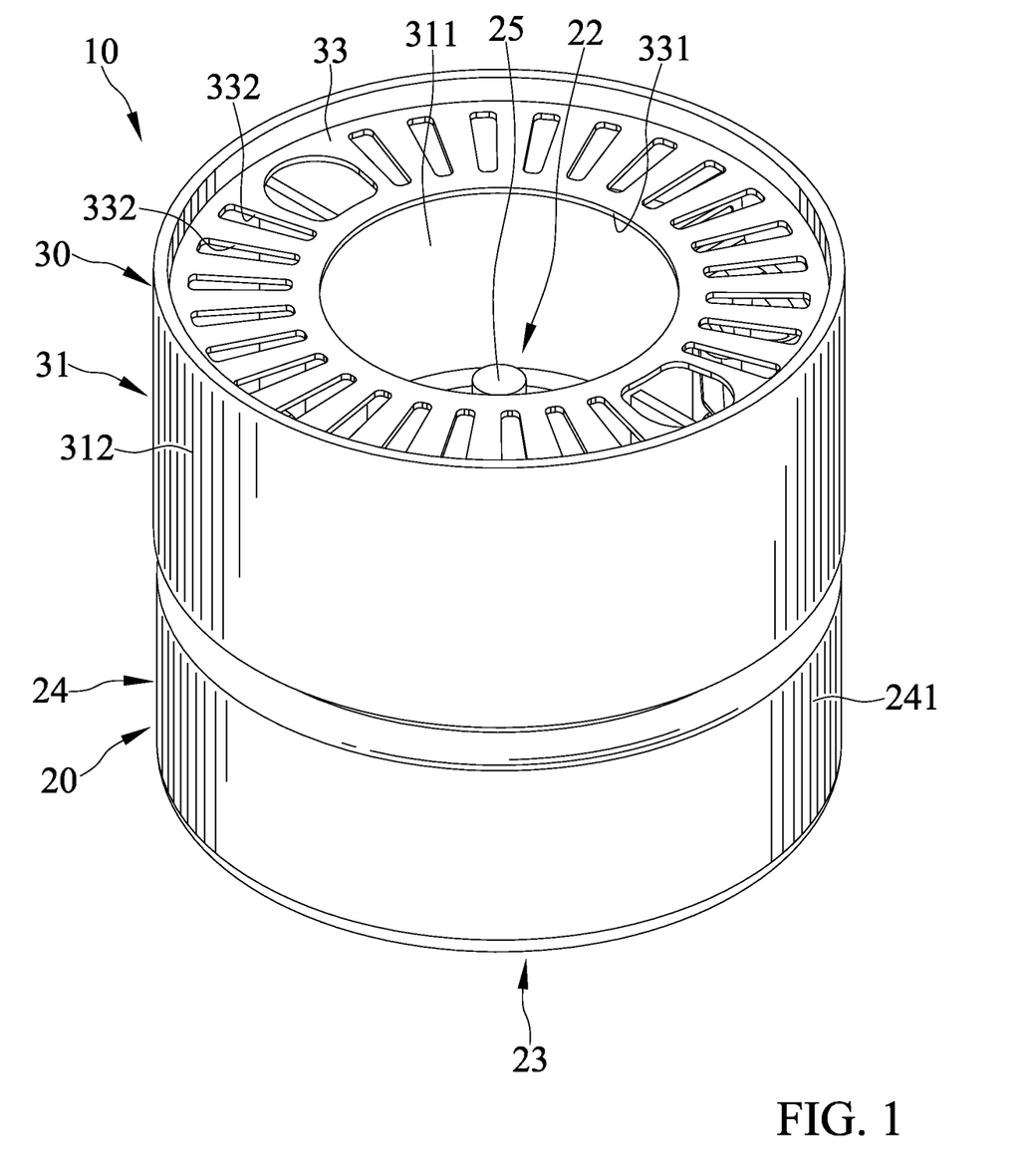
FIG. 1 is a perspective view of a combustion device of a first embodiment according to the present invention.
Figure 2:
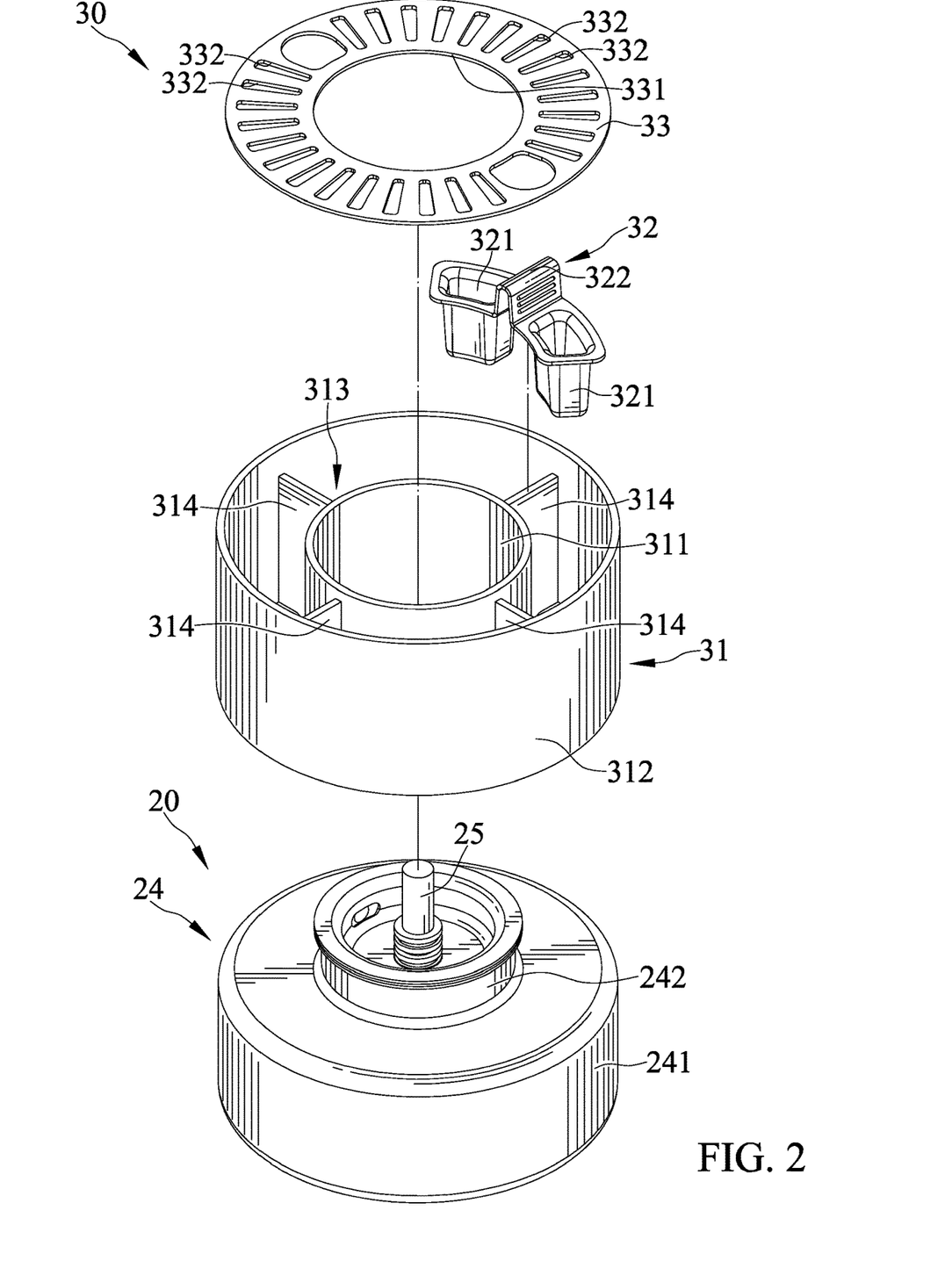
FIG. 2 is an exploded perspective view of the combustion device of FIG. 1.
Figure 3:
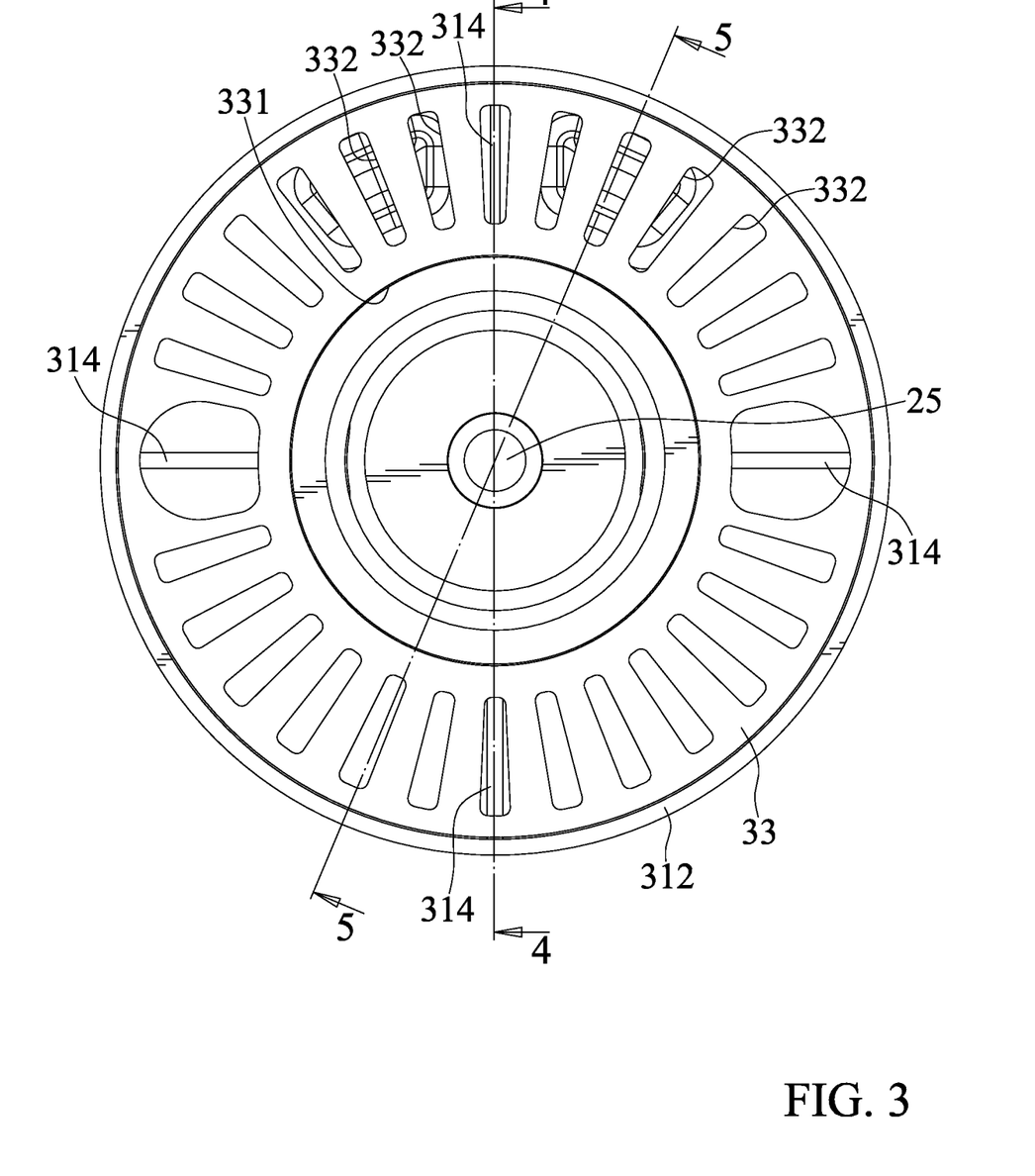
FIG. 3 is a top view of the combustion device of FIG. 1.
Figure 4:
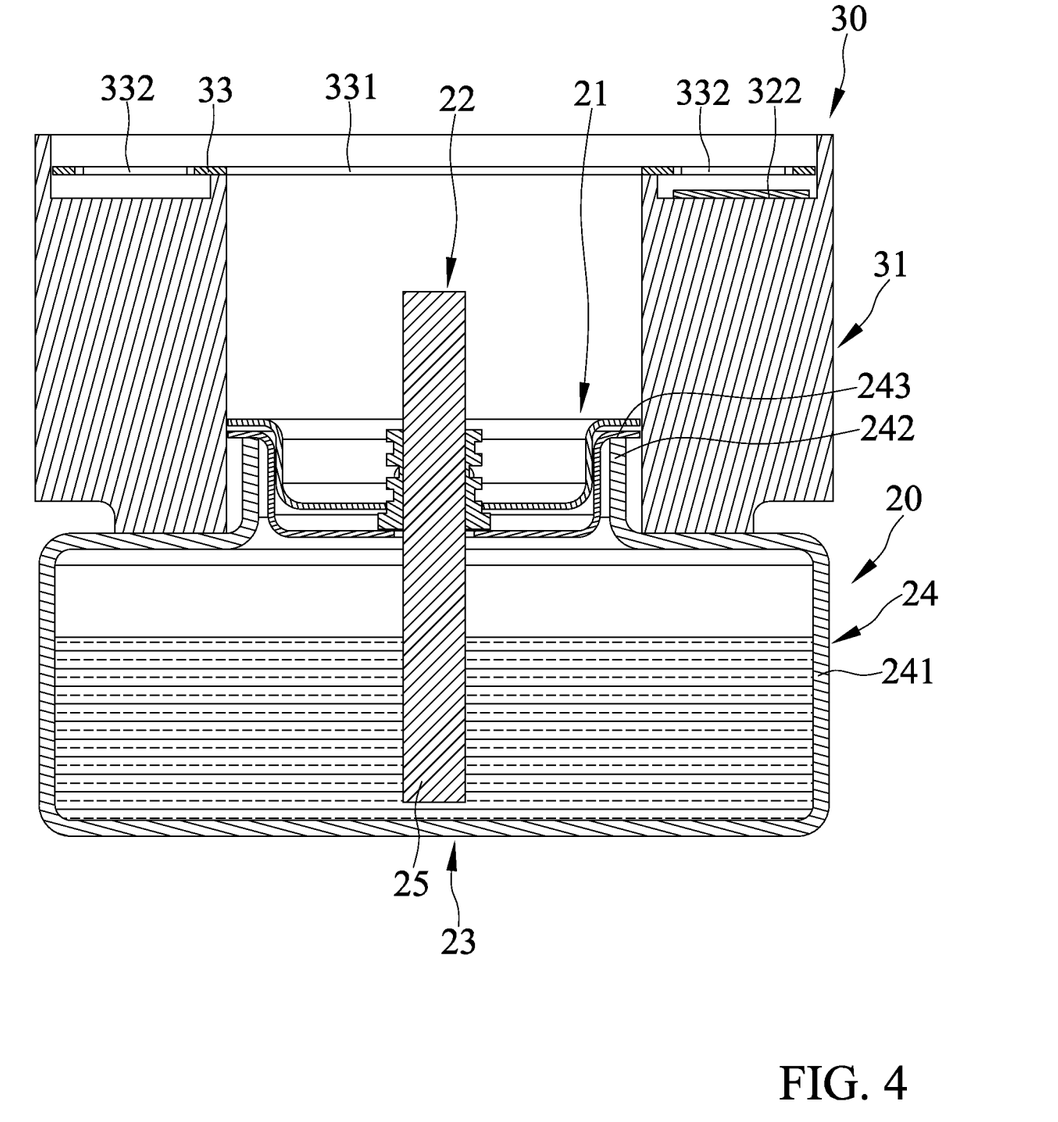
FIG. 4 is a cross-sectional view taken along section line 4-4 of FIG. 3.
Figure 5:
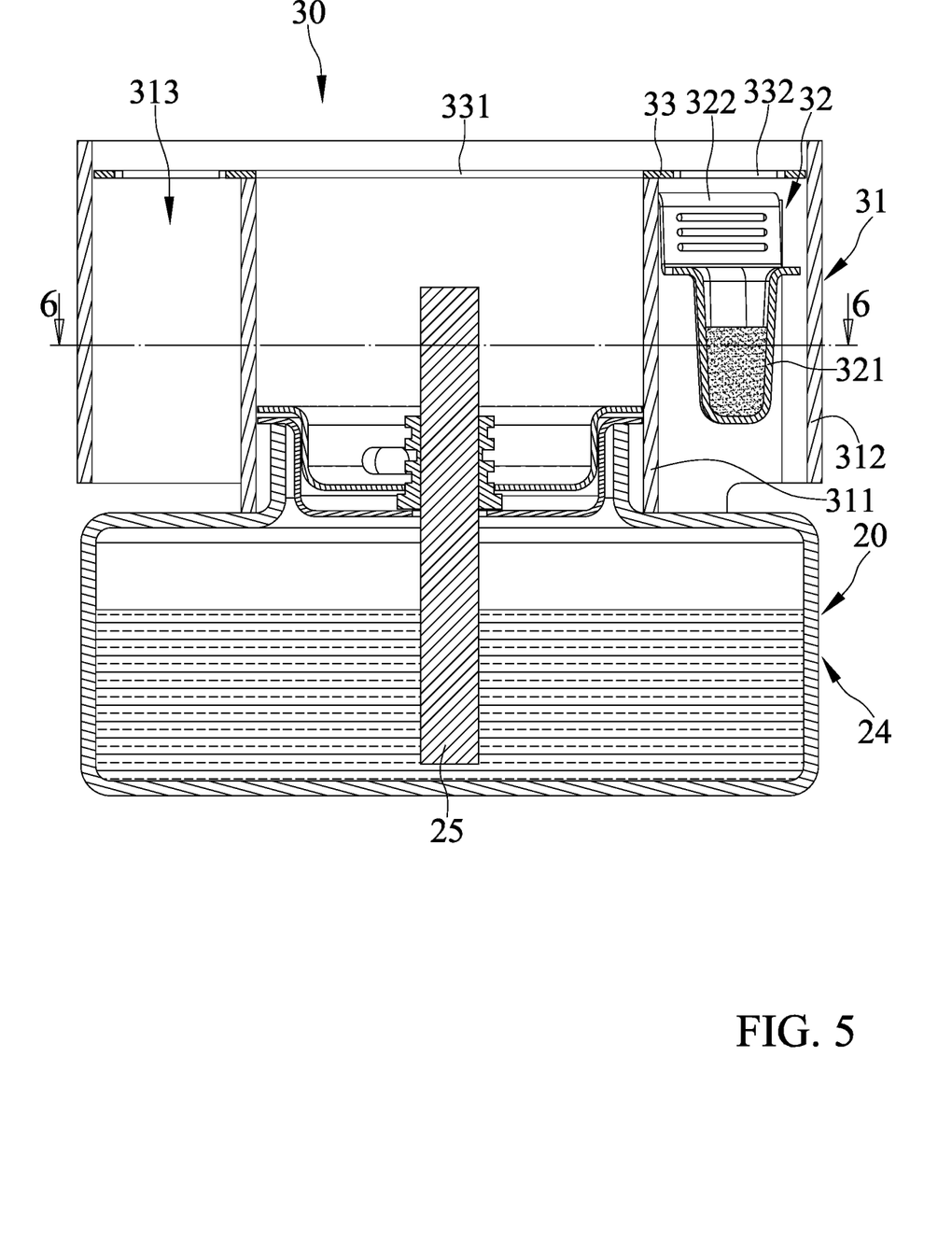
FIG. 5 is a cross-sectional view taken along section line 5-5 of FIG. 3.
Figure 6:
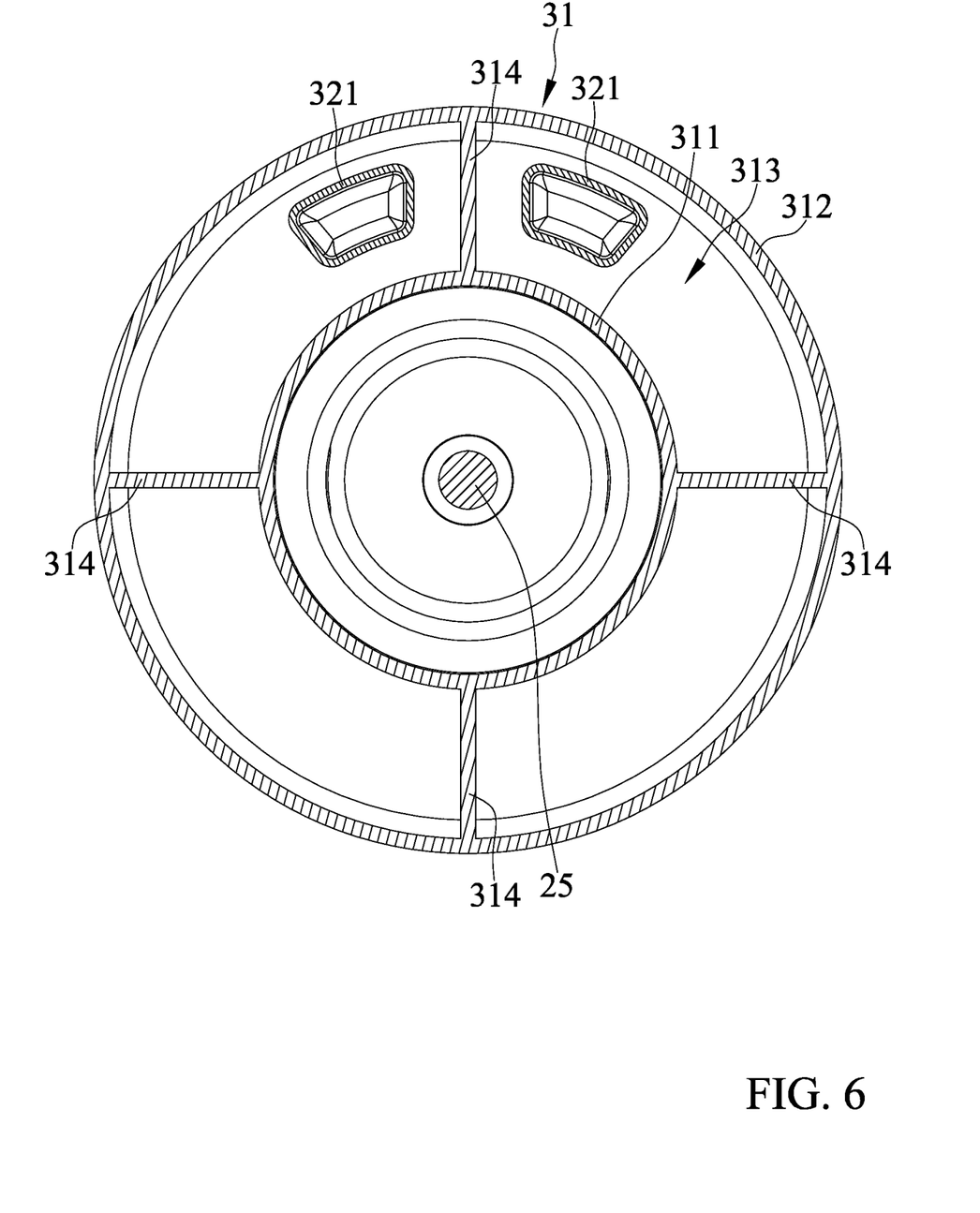
FIG. 6 is a cross-sectional view taken along section line 6-6 of FIG. 5.

FIGS. 1-6 show a combustion device of a first embodiment according to the present invention. The combustion device 10 includes a burner 20 and a fragrance diffuser 30.

The burner 20 is provided with a top end 21 having a combustion portion 22.

The burner 20 is further provided with a bottom end 23 opposite to the top end 21. The burner 20 includes a fuel container 24 and a wick 25. The fuel container 24 includes a wide portion 241 adjacent to the bottom end 23, and a narrow portion 242 adjacent to the top end 21. A width of the narrow portion 242 is less than a width of the wide portion 241 in a horizontal direction. An end of the narrow portion 242 opposite to the wide portion 241 is provided with an opening 243. A first end of the wick 25 is inserted into the fuel container 24 via the opening 243, and a second end of the wick 25 is disposed in the combustion portion 22.

The fragrance diffuser 30 includes a support 31 and a holder 32 adapted to hold a fragrance substance (not shown). The support 31 is disposed on the top end 21 and is provided with an inner wall 311 and an outer wall 312. The inner wall 311 extends in a vertical direction and is arranged around the combustion portion 22 and the narrow portion 242. An end of the inner wall 311 adjacent to the burner 20 is abutted against an outer end face located at a side of the wide portion 241 adjacent to the narrow portion 242. The outer wall 312 extends in the vertical direction and is arranged around the inner wall 311. A holding space 313 is formed between the inner wall 311 and the outer wall 312, and the holder 32 is disposed in the holding space 313.

The support 31 is provided with at least one connection rib 314 extending in the vertical direction and disposed in the holding space 313. A first end of the at least one connection rib 314 is connected to the inner wall 311, and a second end of the at least one connection rib 314 is connected to the outer wall 312 in the horizontal direction. The holder 32 includes two recesses 321, and a hanging portion 322 arranged between the two recesses 321. Two ends of the hanging portion 322 are connected to the two recesses 321, and the hanging portion (322) hangs on a top edge of the at least one connection rib 314 in the vertical direction to cause the two recesses 321 located at two opposite sides of the at least one connection rib 314.

In the embodiment, the support 31 includes four connection ribs 314 respectively extending in the vertical direction and arrayed in the holding space 313 in a circumferential direction at angles of equal intervals. A first end of each connection rib 314 is connected to the inner wall 311, and a second end of each connection rib 314 is connected to the outer wall 312 in the horizontal direction. The hanging portion 322 hangs on a top edge of one of the four connection ribs 314 in the vertical direction to cause the two recesses 321 located at two opposite sides of one of the four connection ribs 314.

Ends of the four connection ribs 314 adjacent to the burner 20 abut against the outer end face located at a side of the wide portion 241 adjacent to the narrow portion 242. The outer wall 312 is not in contact with the fuel container 24. The holding space 313 is communicated with the outside via a gap formed between a bottom edge of the outer wall 312 and the fuel container 24 in the vertical direction.

The fragrance diffuser 30 is further provided with a lid 33 abutting an end of the inner wall 311 opposite to the burner 20 in the vertical direction. The lid 33 is provided with a through hole 331 and a plurality of penetrating holes 332. The through hole 331 corresponds to the combustion portion 22, and an end of the holding space 313 is communicated with the outside via the plurality of penetrating holes 332. An outer periphery of the lid 33 corresponds to an inner periphery of the outer wall 312 in the horizontal direction.

Furthermore, the support 31 may be formed as a single piece. The inner wall 311 and the outer wall 312 may be round tubular and both extend along a central axis. The four connection ribs 314 may be in sheet shapes.

The material of the support 31 can be ceramic, glass or aluminum alloy. After the burner 20 is ignited, the heat generated by the burner 20 raises the temperature of the support 31 to cause the holder 32 also be heated by the burner 20. The fragrance substance, such as fragrance wax in the holder 32 is melted by heat to emit fragrance particles, which pass through the plurality of penetrating holes 332 and is dissipated into the air. Thus, the combustion device 10 is not only for decorative purpose, but also able to emit fragrance. Further, the fragrance diffuser 30 can function as a windshield of the burner 20.

Figure 7:
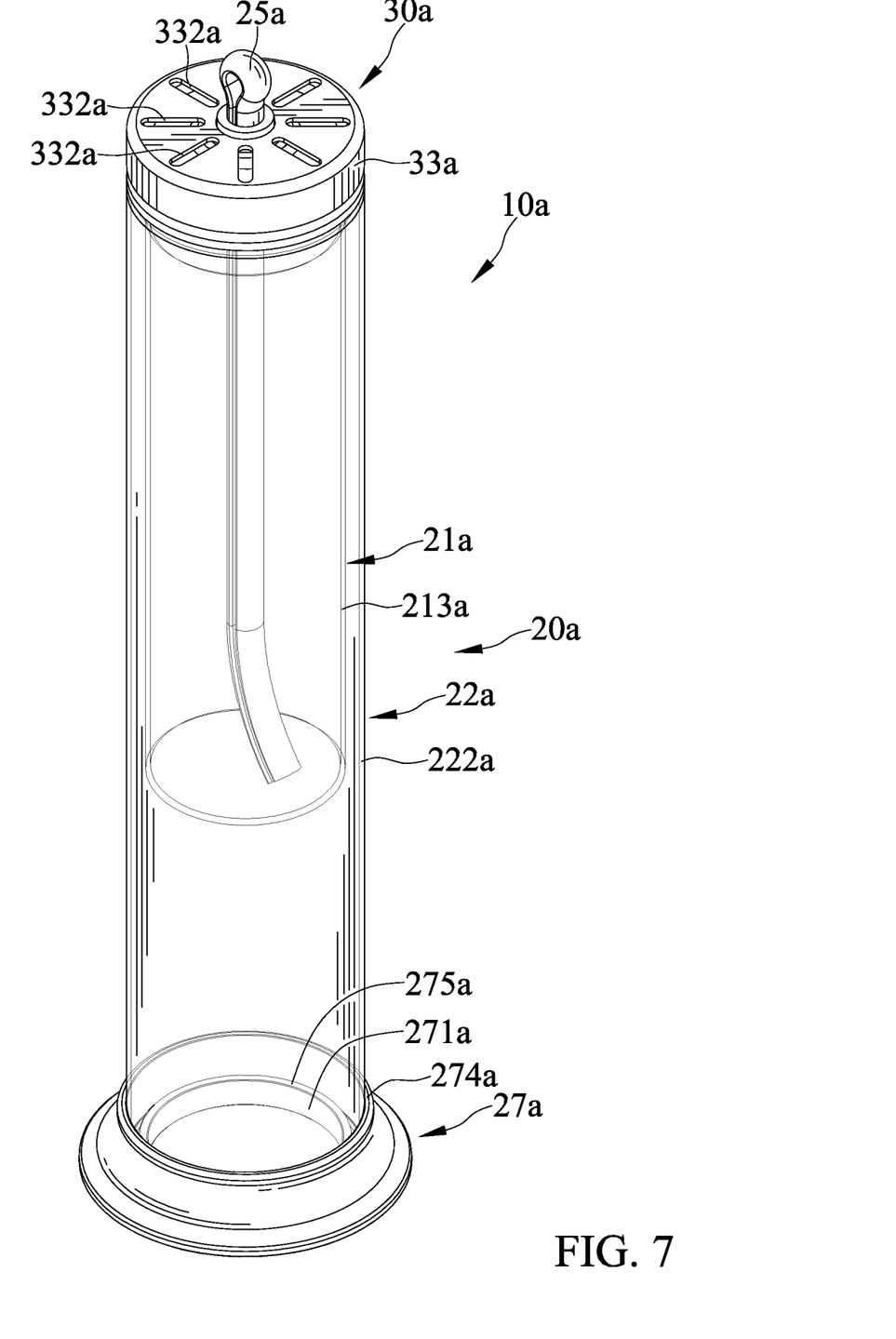
FIG. 7 is a perspective view of a combustion device of a second embodiment according to the present invention.
Figure 8:
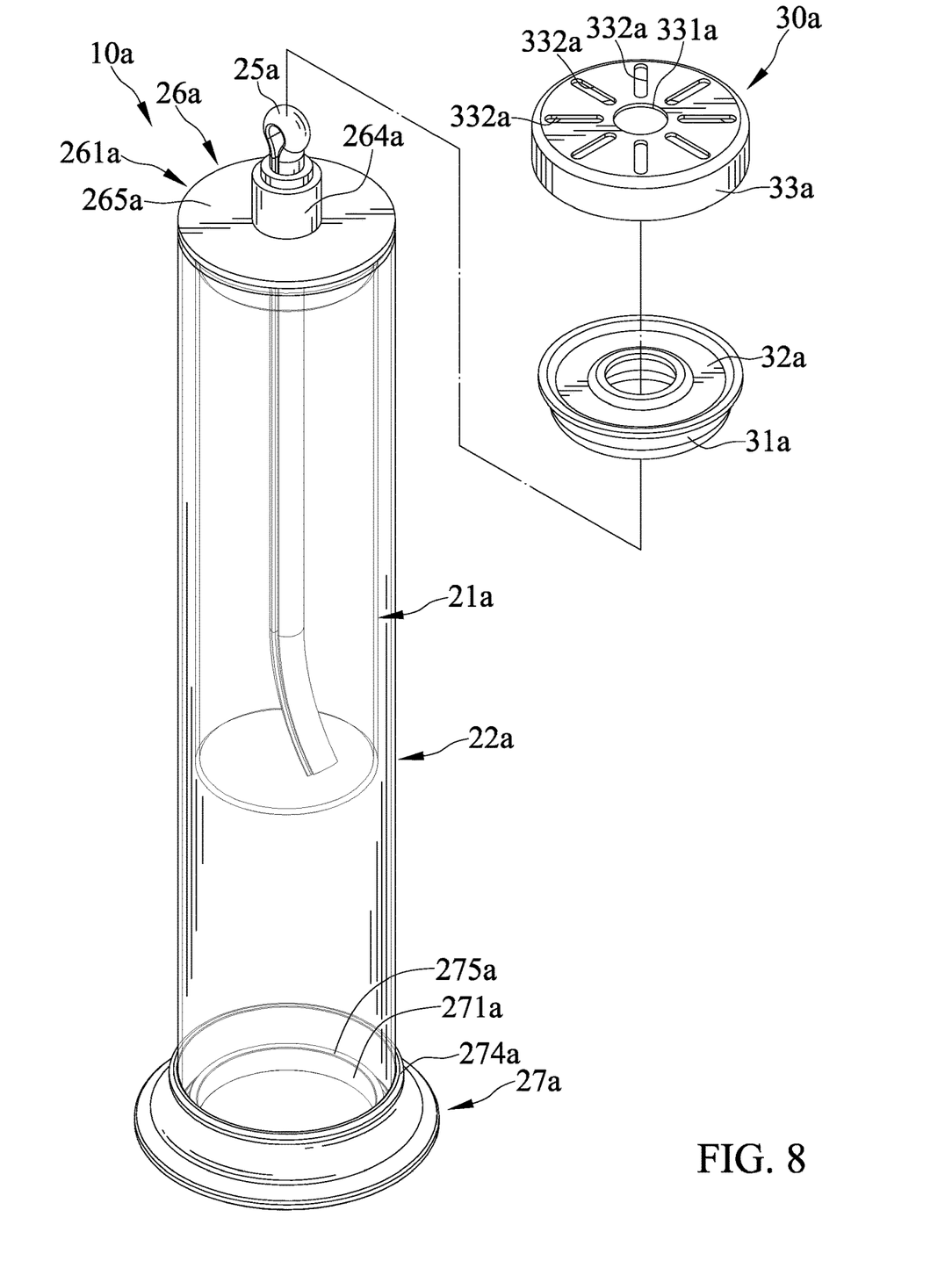
FIG. 8 is an exploded perspective view of the combustion device of FIG. 7.
Figure 9:
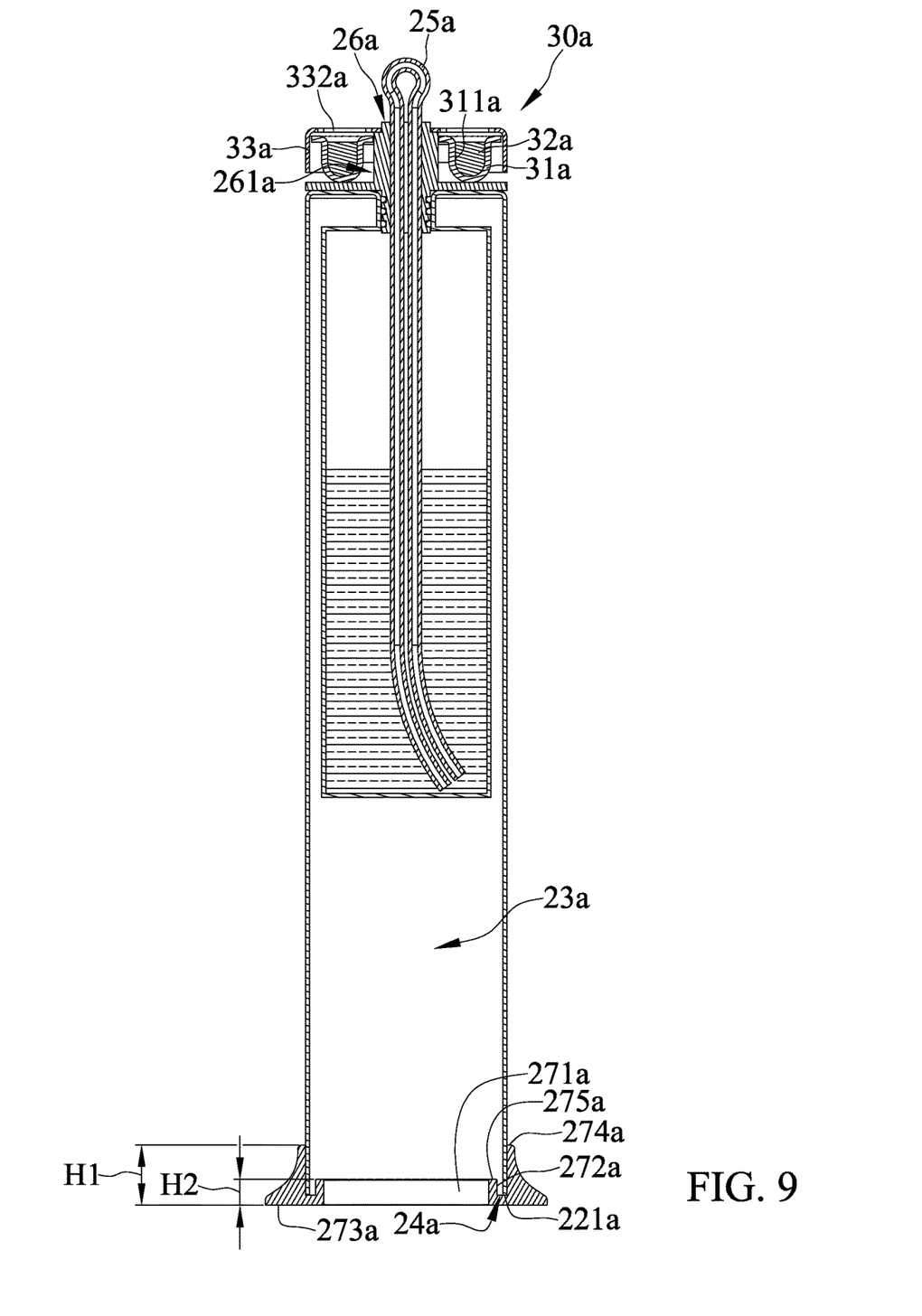
FIG. 9 is a cross-sectional view of the combustion device of FIG. 7.
Figure 10:
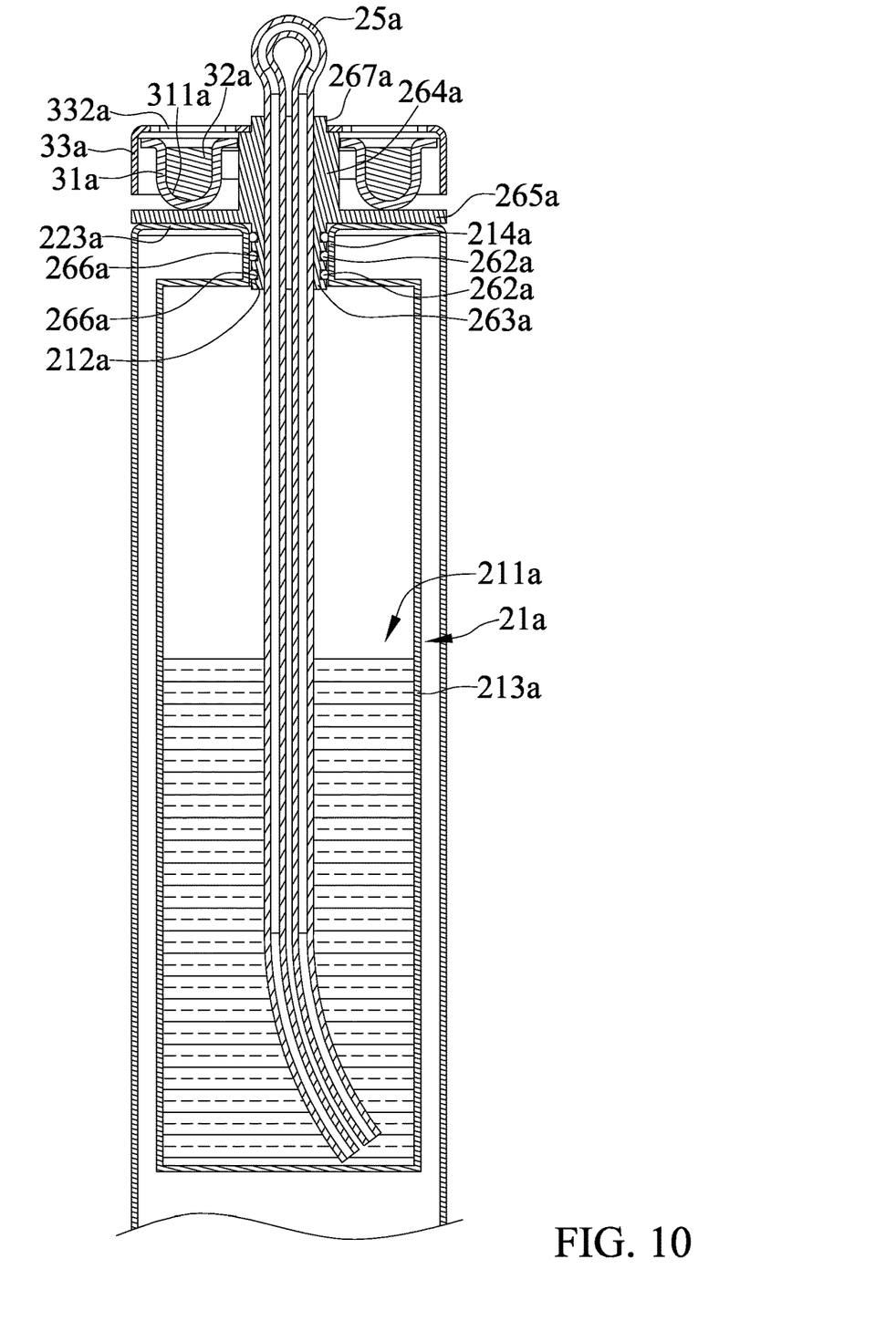
FIG. 10 is an enlarged view of the combustion device of FIG. 9.

FIGS. 7-10 show a combustion device of a second embodiment according to the present invention. The combustion device 10a includes a burner 20a and a fragrance diffuser 30a.

The burner 20a includes an inner wall 21a and an outer wall 22a. The inner wall 21a provided with a fuel container 211a and an opening 212a communicated with the fuel container 211a. The outer wall 22a is arranged around the inner wall 21a, and a hollow space 23a is formed between the inner wall 21a and the outer wall 22a. The inner wall 21a and the outer wall 22a may be formed as a single piece, and the inner wall 21a and the outer wall 22a are made of glass and are transparent. A bottom edge 221a of the outer wall 22a is provided with an aperture 24a communicated with the hollow space (23a) in a vertical direction.

An inner periphery of the outer wall 22a is not in contact with an outer periphery of the inner wall 21a. The inner wall 21a includes a tubular containing portion 213a and a connection tube portion 214a. The fuel container 211a is disposed in the containing portion 213a. The connection tube portion 214a is connected to the containing portion 213a. The opening 212a is disposed in the connection tube portion 214a. The outer wall 22a includes an outer tubular portion 222a and a connection portion 223a. The containing portion 213a and the outer tubular portion 222a both extend along a central axis. A first side of the connection portion 223a is connected to an end of the connection tube portion 214a opposite to the containing portion 213a, and a second side of the connection portion 223a is connected to a top end of the outer tubular portion 222a in the vertical direction.

The burner 20a further includes a wick 25a and a collar assembly 26a. The wick 25a is inserted into the fuel container 211a via the opening 212a, and the wick 25a may be made of metal.

The collar assembly 26a includes a ring body 261a and a plurality of O-rings 262a. The ring body 261a is formed as a single piece and includes a lower tube portion 263a, an upper tube portion 264a, and a flange 265a. The lower tube portion 263a and the upper tube portions 264a are mounted around the wick 25a. The lower tube portion 263a is inserted into the opening 212a. The upper tube portion 264a extends out of the opening 212a and is connected with the lower tube portion 263a. The flange 265a is radially connected outer peripheries of the lower tube portion 263a and the upper tube portions 264a and is disposed between the lower tube portion 263a and the upper tube portions 264a. Further, the lower tube portion 263a and the upper tube portions 264a may be round tubular and both extend along a central axis. The flange 265a may be an annular sheet.

An outer periphery of the lower tube portion 263a opposite to the wick 25a is provided with a plurality of grooves 266a, and the plurality of the O-rings 262a are respectively arranged in the plurality of grooves 266a. Sides of the plurality of the O-rings 262a opposite to the ring body 261a abut against an inner periphery of the connection tube portion 214a. Further, the ring body 261a may be made of metal or plastic.

An end of the upper tube portion 264a opposite to the lower tube portion 263a is provided with a neck 267a. A width of the neck 267a is less than a maximum width of the upper tube portion 264a in a radial direction.

The burner 20a is connected to a base 27a mounted with the aperture 24a. The base 27a is provided with an open hole 271a communicated with the hollow space 23a. A first side of the base 27a is provided with a slot 272a disposed around the open hole 271a, and the bottom edge 221a is inserted into the slot 272a.

A second side of the base 27a is provided with a bottom portion 273a. A first side of the slot 272a opposite to the open hole 271a is provided with an outer edge 274a, and a first height H1 is formed between the outer edge 274a and the bottom portion 273a in the vertical direction. A second side of the slot 272a adjacent to the open hole 271a is provided with an inner edge 275a, and a second height H2 is formed between the inner edge 275a and the bottom portion 273a in the vertical direction, and the second height H2 is less than the first height H1.

The fragrance diffuser 30a is mounted on a side of the flange 265a opposite to the lower tube portion 263a and is disposed adjacent to an outer periphery of the upper tube portion 264a.

The fragrance diffuser 30a includes a holder 31a, a fragrance substance 32a, and a lid 33a. The holder 31a is mounted on the side of the flange 265a opposite to the lower tube portion 263a and is disposed adjacent to the upper tube portion 264a. A side of the holder 31a opposite to the flange 265a is provided with a recess 311a, and the fragrance substance 32a is disposed in the recess 311a. The lid 33a is disposed on the side of the holder 31a opposite to the flange 265a and is provided with a through hole 331a and a plurality of penetrating holes 332a. The through hole 331a is mounted around the upper tube portion 264a, and the plurality of penetrating holes 332a correspond to the recess 311a. Further, the lid 33a may be mounted around the neck 267a to abut against a stepped end face of the neck 267a adjacent to the upper tube portion 264a.

After the burner 20a is ignited, the heat generated by the burner 20a raises the temperature of the ring body 261a to cause the holder 31a also be heated by the burner 20a. The fragrance substance 32a, such as fragrance wax in the holder 31a is melted by heat to emit fragrance particles, which pass through the plurality of penetrating holes 332a and is dissipated into the air. Thus, the combustion device 10a is not only for decorative purpose, but also able to emit fragrance.

The combustion device 10a can achieve a good heat insulation effect by a two-layer structure formed from the inner wall 21a and the outer wall 22a. Although the center of gravity of the two-layer structure of the burner 20a will be slightly higher, but the base 27a mounted on the bottom edge 221a of the burner 20a can lower the center of gravity of the burner 20a to prevent the combustion device 10a being tipped over. Moreover, the most fragile position of the glass material is at the edges and the corners, so that the bottom edge 221a is covered by the base 27a to prevent the burner 20a being easily damaged.

While various embodiments have been described above, it should be understood that they have been presented by way of example only, and not limitation. For example, any of the elements associated with the privacy summary may employ any of the desired functionality set forth hereinabove. Thus, the breadth and scope of a preferred embodiment should not be limited by any of the above-described exemplary embodiments.

What is claimed is:

1. A combustion device comprising:
   a burner provided with a top end having a combustion portion, wherein the burner is provided with a bottom end opposite to the top end, wherein the burner includes a fuel container and a wick, wherein the fuel container includes a wide portion adjacent to the bottom end, and a narrow portion adjacent to the top end, wherein a width of the narrow portion is less than a width of the wide portion in a horizontal direction, wherein an end of the narrow portion opposite to the wide portion is provided with an opening, wherein a first end of the wick is inserted into the fuel container via the opening, wherein a second end of the wick is disposed in the combustion portion; and
   a fragrance diffuser including a support and a holder adapted to hold a fragrance substance, wherein the support is disposed on the top end and provided with an inner wall and an outer wall, wherein the inner wall extends in a vertical direction and is arranged around the combustion portion, wherein the outer wall extends in the vertical direction and arranged around the inner wall, wherein a holding space is formed between the inner wall and the outer wall, wherein the holder is disposed in the holding space, wherein the inner wall is arranged around the narrow portion, wherein an end of the inner wall adjacent to the burner is abutted against an outer end face located at a side of the wide portion adjacent to the narrow portion,
   wherein the support is provided with at least one connection rib extending in the vertical direction and disposed in the holding space, wherein a first end of the at least one connection rib is connected to the inner wall, wherein a second end of the at least one connection rib is connected to the outer wall in the horizontal direction, wherein the holder includes two recesses, and a hanging portion arranged between the two recesses, wherein two ends of the hanging portion are connected to the two recesses, wherein the hanging portion hangs on a top edge of the at least one connection rib in the vertical direction, and wherein the two recesses are located at two opposite sides of the at least one connection rib.

2. The combustion device as claimed in claim 1, wherein the support includes four connection ribs respectively extending in the vertical direction and arrayed in the holding space in a circumferential direction at angles of equal intervals, wherein a first end of each connection rib is connected to the inner wall, wherein a second end of each connection rib is connected to the outer wall in the horizontal direction, wherein the hanging portion hangs on a top edge of one of the four connection ribs in the vertical direction, and wherein the two recesses are located at two opposite sides of one of the four connection ribs.

3. The combustion device as claimed in claim 2, wherein ends of the four connection ribs adjacent to the burner abut against the outer end face located at a side of the wide portion adjacent to the narrow portion, wherein the outer wall is not in contact with the fuel container, and wherein the holding space is communicated with the outside via a gap formed between a bottom edge of the outer wall and the fuel container in the vertical direction.

4. The combustion device as claimed in claim 1, wherein the fragrance diffuser is provided with a lid abutting an end of the inner wall opposite to the burner in the vertical direction, wherein the lid is provided with a through hole and a plurality of penetrating holes, wherein the through hole corresponds to the combustion portion, and wherein an end of the holding space is communicated with the outside via the plurality of penetrating holes.

5. The combustion device as claimed in claim 4, wherein an outer periphery of the lid corresponds to an inner periphery of the outer wall in the horizontal direction.

6. The combustion device as claimed in claim 3, wherein the support is formed as a single piece, wherein the inner wall and the outer wall are round tubular and both extend along a central axis, and wherein the four connection ribs are sheet shapes.

7. A combustion device comprising:
   a burner provided with a fuel container and an opening communicated with the fuel container, with the burner including a wick and a collar assembly, with the wick inserted into the fuel container via the opening, with a ring body of the collar assembly including a lower tube portion, an upper tube portion, and a flange, with the lower tube portion and the upper tube portion mounted around the wick, with the lower tube portion inserted into the opening, with the upper tube portion extending out of the opening and connected with the lower tube portion, with the flange radially connected to outer peripheries of the lower tube portion and the upper tube portion and disposed between the lower tube portion and the upper tube portion, wherein the burner includes an inner wall and an outer wall, wherein the fuel container and the opening are disposed at the inner wall, wherein the outer wall is arranged around the inner wall, wherein a hollow space is formed between the inner wall and the outer wall, wherein a bottom edge of the outer wall is provided with an aperture communicated with the hollow space in a vertical direction; and
   a fragrance diffuser mounted on a side of the flange opposite to the lower tube portion and disposed adjacent to an outer periphery of the upper tube portion.

8. The combustion device as claimed in claim 7, wherein the fragrance diffuser includes a holder, a fragrance substance, and a lid, wherein the holder is mounted on the side of the flange opposite to the lower tube portion and disposed adjacent to the upper tube portion, wherein a side of the holder opposite to the flange is provided with a recess, wherein the fragrance substance is disposed in the recess, wherein the lid is disposed on the side of the holder opposite to the flange and is provided with a through hole and a plurality of penetrating holes, wherein the through hole is mounted around the upper tube portion, and wherein the plurality of penetrating holes correspond to the recess.

9. The combustion device as claimed in claim 8, wherein an end of the upper tube portion opposite to the lower tube portion is provided with a neck, wherein a width of the neck is less than a maximum width of the upper tube portion in a radial direction, and wherein the lid is mounted around the neck and abuts against a stepped end face of the neck adjacent to the upper tube portion.

10. The combustion device as claimed in claim 8, wherein the ring body is formed as a single piece, wherein the lower tube portion and the upper tube portion are round tubular and both extend along a central axis, and wherein the flange is an annular sheet.

11. The combustion device as claimed in claim 7, wherein the burner is connected to a base mounted with the aperture, wherein the base is provided with an open hole communicated with the hollow space, wherein a first side of the base is provided with a slot disposed around the open hole, and wherein the bottom edge is inserted into the slot.

12. The combustion device as claimed in claim 11, wherein a second side of the base is provided with a bottom portion, wherein a first side of the slot opposite to the open hole is provided with an outer edge, wherein a first height is formed between the outer edge and the bottom portion in the vertical direction, wherein a second side of the slot adjacent to the open hole is provided with an inner edge, wherein a second height is formed between the inner edge and the bottom portion in the vertical direction, and wherein the second height is less than the first height.

13. The combustion device as claimed in claim 11, wherein the inner wall and the outer wall are formed as a single piece.

14. The combustion device as claimed in claim 11, wherein an inner periphery of the outer wall is not in contact with an outer periphery of the inner wall, wherein the inner wall includes a tubular containing portion and a connection tube portion, wherein the fuel container is disposed in the containing portion, wherein the connection tube portion is connected to the containing portion, wherein the opening is disposed in the connection tube portion, wherein the outer wall includes an outer tubular portion and a connection portion, wherein the containing portion and the outer tubular portion both extend along a central axis, wherein a first side of the connection portion is connected to an end of the connection tube portion opposite to the containing portion, and wherein a second side of the connection portion is connected to a top end of the outer tubular portion in the vertical direction.

15. The combustion device as claimed in claim 14, wherein the collar assembly includes a plurality of O-rings, wherein an outer periphery of the lower tube portion opposite to the wick is provided with a plurality of grooves, wherein the plurality of the O-rings are respectively arranged in the plurality of grooves, and wherein sides of the plurality of the O-rings opposite to the ring body abut against an inner periphery of the connection tube portion.

16. The combustion device as claimed in claim 11, wherein the inner wall and the outer wall are made of glass and are transparent, wherein the wick is made of metal, and wherein the ring body is made of metal or plastic.

* * * * *